United States Patent
Tsuji

(10) Patent No.: US 9,697,923 B2
(45) Date of Patent: Jul. 4, 2017

(54) RADIATION IMAGE CAPTURING SYSTEM

(71) Applicant: FUJIFILM Corporation, Tokyo (JP)

(72) Inventor: Tetsuya Tsuji, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 174 days.

(21) Appl. No.: 14/799,004

(22) Filed: Jul. 14, 2015

(65) Prior Publication Data
US 2016/0035451 A1    Feb. 4, 2016

(30) Foreign Application Priority Data

Jul. 31, 2014   (JP) .................... 2014-156941

(51) Int. Cl.
*G01N 23/04* (2006.01)
*G21K 4/00* (2006.01)
*A61B 6/00* (2006.01)

(52) U.S. Cl.
CPC .............. *G21K 4/00* (2013.01); *A61B 6/4266* (2013.01); *A61B 6/4283* (2013.01); *A61B 6/4291* (2013.01); *A61B 6/4452* (2013.01); *A61B 6/5241* (2013.01); *G21K 2004/02* (2013.01)

(58) Field of Classification Search
CPC ... G21K 1/00; G21K 1/10; G01T 1/20; G01T 1/2006; G01T 1/2928; G01T 1/2018; G01N 23/04; A61B 6/4233; A61B 6/4266; A61B 6/4283; A61B 6/4291; A61B 6/585
USPC .......................... 378/62, 98.8, 154, 156, 207
See application file for complete search history.

(56) References Cited

U.S. PATENT DOCUMENTS

2004/0071269 A1    4/2004  Wang et al.

FOREIGN PATENT DOCUMENTS

JP    2004-160208 A    6/2004

*Primary Examiner* — Jurie Yun
(74) *Attorney, Agent, or Firm* — Birch, Stewart, Kolasch & Birch, LLP

(57) ABSTRACT

A radiation image capturing system capable of improving image quality of a radiation image is provided. A position of a joint of a grid is determined in consideration of displacement of an angle of incidence of radiation on a grid unit and a radiation detector group, and a joint image caused by the joint of the grid is prevented from being included in a search range of a position of a boundary in the radiation image captured by the radiation detector. The joint of the grid is provided in a position away $\pm(y1+2 \times y2) \times \tan\beta$ or more from a position of a step of the radiation detector.

20 Claims, 10 Drawing Sheets

RADIATION IMAGE CAPTURING SYSTEM 10

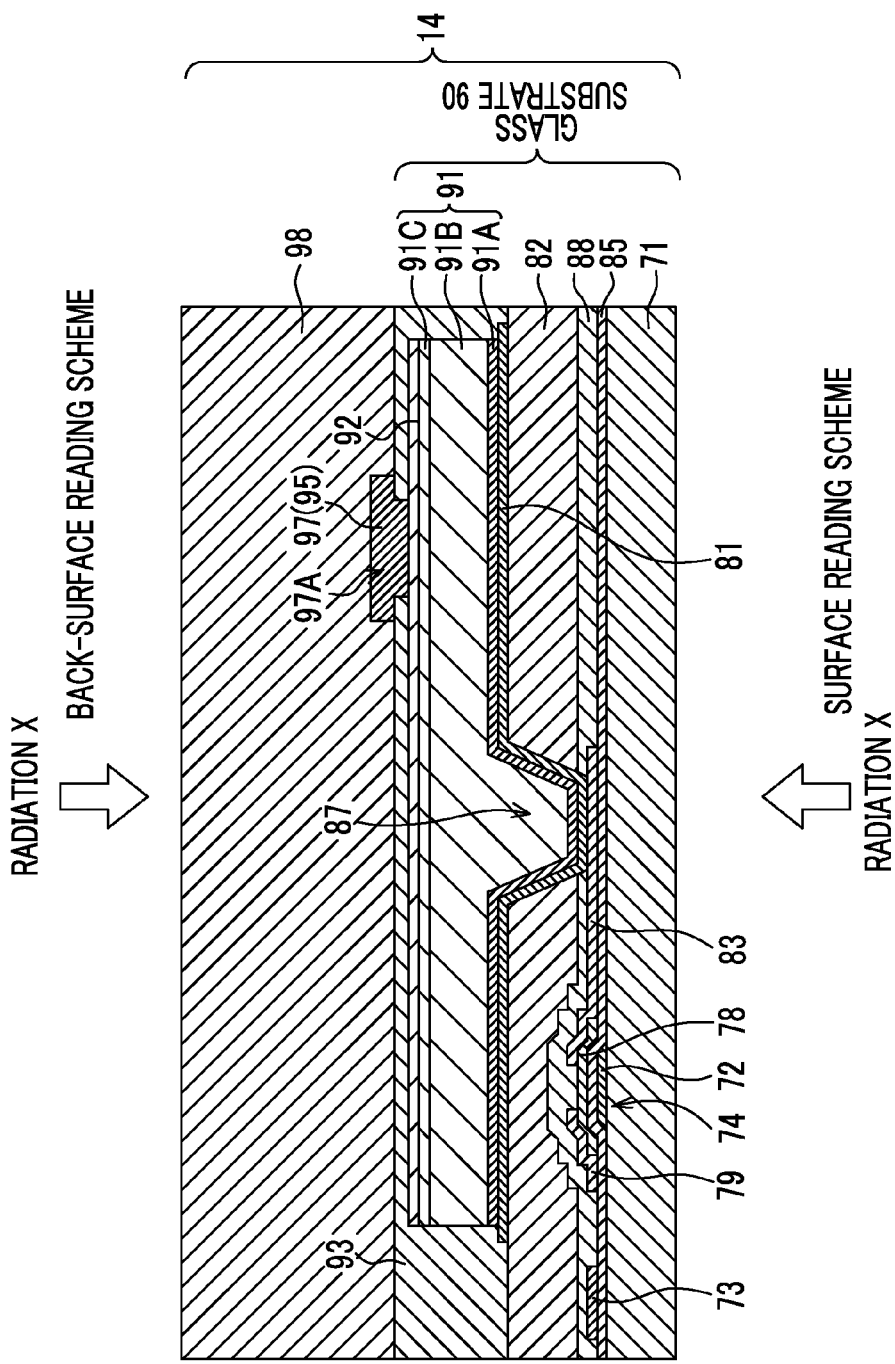

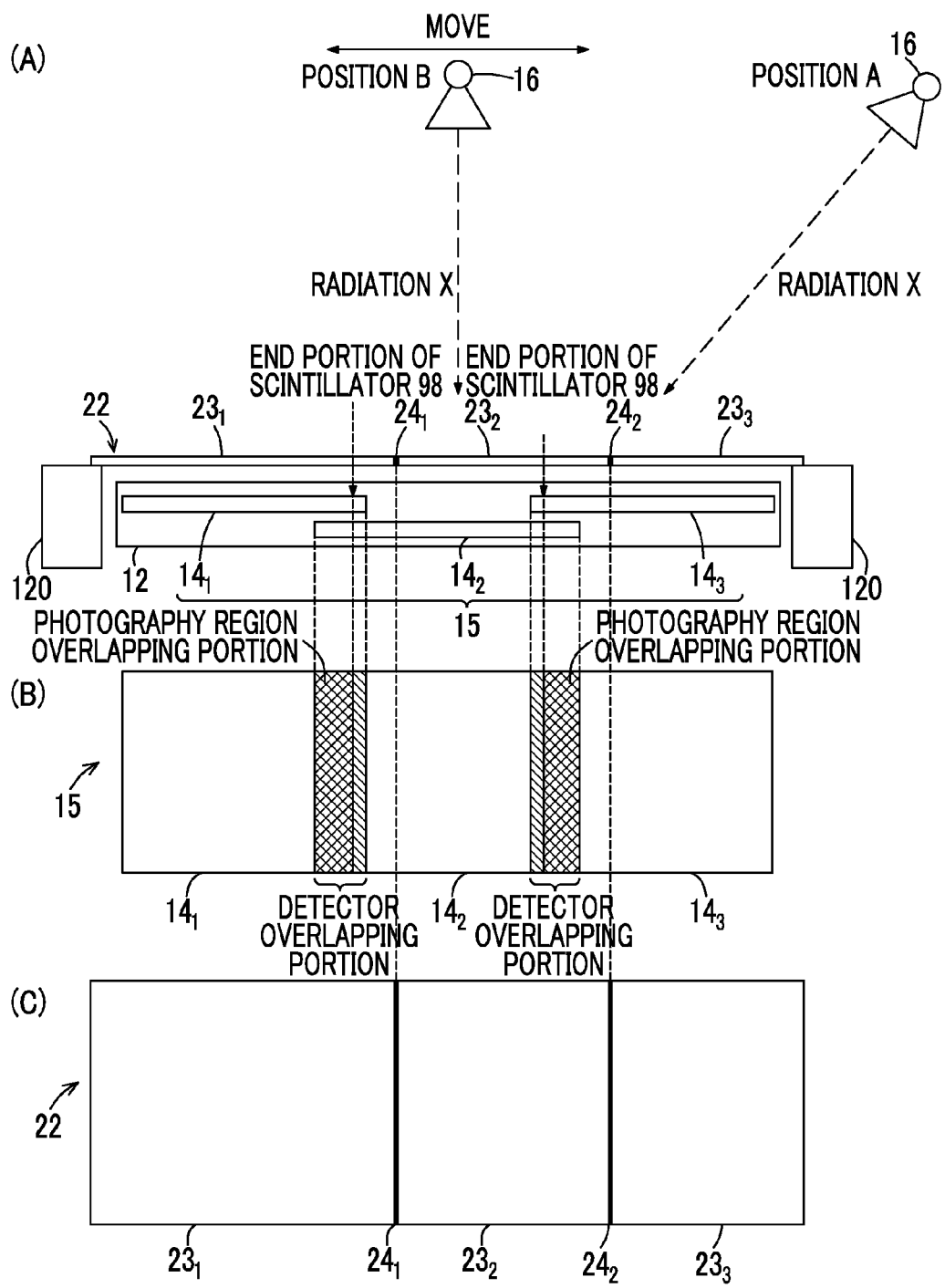

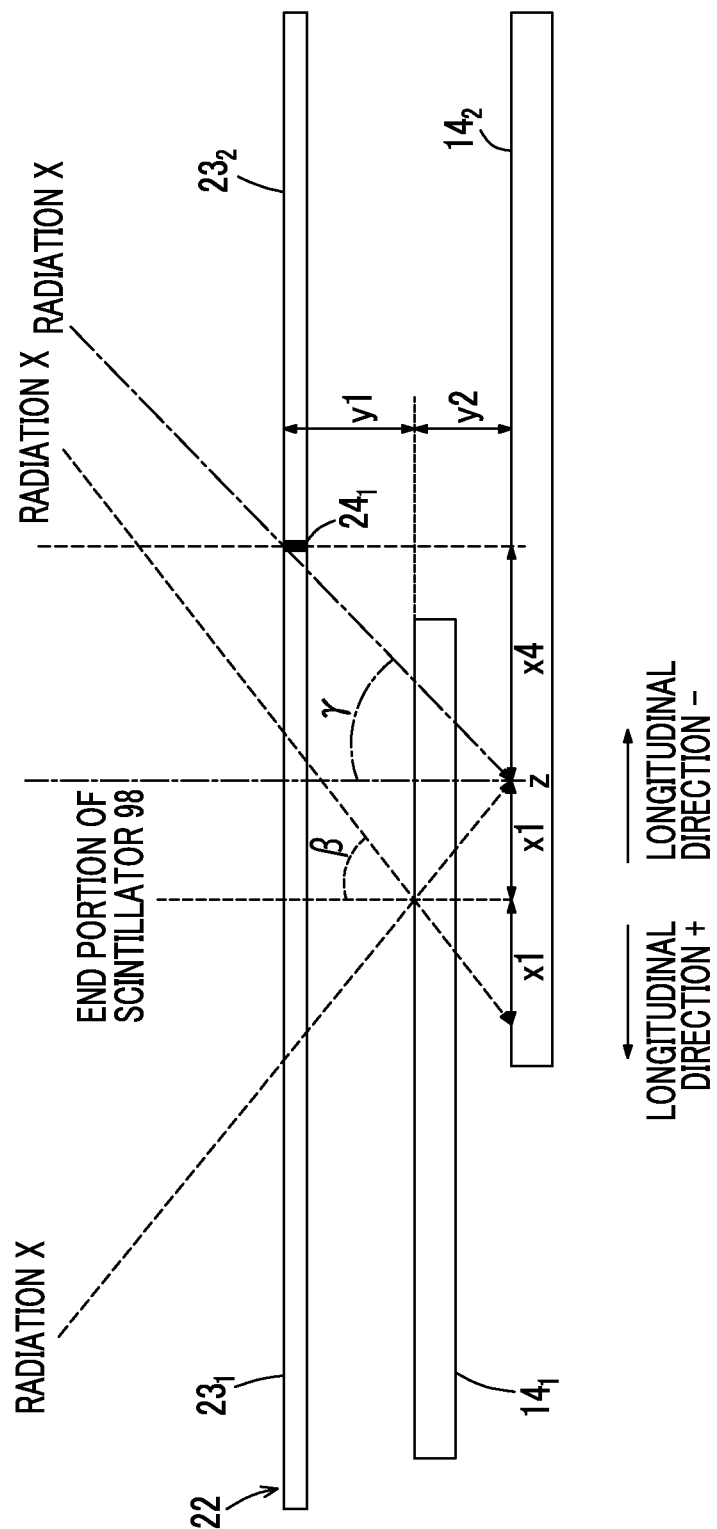

RADIATION IMAGE CAPTURING SYSTEM

CROSS-REFERENCE TO RELATED APPLICATIONS

The present application claims priority under 35 U.S.C. §119 to Japanese Patent Application No. 2014-156941, filed on Jul. 31, 2014. Each of the above application(s) is hereby expressly incorporated by reference, in its entirety, into the present application.

BACKGROUND OF THE INVENTION

1. Field of the Invention

The present invention relates to a radiation image capturing system.

2. Description of the Related Art

For example, a radiation image capturing system that performs radiation photography aiming at medical diagnostics is conventionally known as a radiation image capturing system that captures a radiation image of a photography target. The radiation image capturing system includes a radiation detector, and captures a radiation image by detecting radiation radiated from a radiation irradiation device and transmitted through a subject using the radiation detector. The radiation detector performs capturing of the radiation image by collecting and reading charge generated by the radiated radiation.

A technology for performing photography using a plurality of radiation detectors, for example, to photograph a large photography target such as a long photography target is known. For example, a technology in which storage phosphor screens of CR (Computed Radiography) cassettes are used as radiation detectors, and end portions of a plurality of adjacent CR cassettes (storage phosphor screens) overlap, so as to capture a radiation image of an elongated object is described in JP2004-160208A.

In general, when the radiation image is captured, the radiation is transmitted through the photography target, and scattering rays are generated. Thus, the scattered rays are included in the radiation transmitted through the photography target. Therefore, a grid that eliminates the scattered rays is provided between the photography target and the radiation detector so as to eliminate the scattered rays included in the radiation reaching the radiation detector. By eliminating the scattered rays, effects such as suppression of degradation of a contrast of the radiation image are obtained, and image quality of the radiation image is improved.

In the technology described in JP2004-160208A, an anti-scatter grid is arranged between the CR cassettes and a patient that is the photography target to cover all of the plurality of overlapping CR cassettes.

In the case where the end portions of the radiation detectors overlap and photography is performed as described above, a shadow of the radiation detector on the upper side (a side close to a radiation irradiation device) may be shown as a step image in the radiation image captured by the radiation detector on the lower side (a side far from the radiation irradiation device).

Further, in the case where such photography is performed, a plurality of grids are jointed and used. In the case where the plurality of grids are jointed together and used, a joint of the grids is projected on the radiation detector. Accordingly, a joint image caused by the joint of the grid may be shown on the captured radiation image.

Therefore, both the step image and the joint image may be included in the radiation image. The step image is corrected through image processing, but in the case where both the step image and the joint image are included in one radiation image, correction of the step image and the joint image cannot be appropriately corrected, and image quality of the radiation image may be degraded.

SUMMARY OF THE INVENTION

An object of the present invention is to provide a radiation image capturing system capable of improving image quality of a radiation image.

According to an aspect of the invention, there is provided a radiation image capturing system including an irradiation unit that irradiates a photography target with radiation; a grid unit that removes scattered rays included in the radiation transmitted through the photography target, the grid unit including a plurality of jointed grids; and a radiation detector group that includes a plurality of radiation detectors arranged side by side in a direction intersecting an incidence direction of the radiation in a state in which end portions of the radiation detectors overlap in the incidence direction, and captures a radiation image according to the radiation, the radiation image including a step image caused by a step with respect to the incidence direction in the end portion, and a joint image caused by a joint of the grid, in which a position in which the joint of the grid is provided is a position in which a first region including the step image of the radiation image and a second region including the joint image are spaced.

In the radiation image capturing system, the positions of the first region, and the second region included in the radiation image may be determined based on an angle of incidence of the radiation on the radiation detector.

In the radiation image capturing system, the first region may be a search range in which a correction unit searches for the radiation image, the correction unit searching a search range of the radiation image to detect a position of the step image and correcting the detected step image.

In the radiation image capturing system, the correction unit may detect the position of the step image based on a position of a boundary between the step image included in the radiation image and an image different from the step image.

The radiation image capturing system may further include the correction unit.

In the radiation image capturing system, the search range may be determined in advance based on a thickness in the incidence direction of the radiation detector provided on the side close to the irradiation unit in the incidence direction, a distance between the corresponding radiation detector and the radiation detector overlapping the corresponding radiation detector, a position of the step, and the angle of incidence of the radiation on the radiation detector.

In the radiation image capturing system, a position of the joint of the grid unit may be a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and an angle of incidence of the radiation on the radiation detector.

In the radiation image capturing system, the joint may extend in a direction along the step.

In the radiation image capturing system, the radiation detector group may include a first radiation detector that captures a radiation image in which the step image is not included; and a second radiation detector that is arranged in a position farther from the irradiation unit than the first radiation detector, and captures a radiation image including the step image and the joint image.

In the radiation image capturing system, the radiation detector may include a scintillator that converts radiation radiated from the irradiation unit into light; a sensor unit that generates charge according to an amount of light converted by the scintillator; and a substrate in which a plurality of pixels are formed, the pixel including a switch element for reading the charge from the sensor unit.

In the radiation image capturing system, the scintillator is formed with a smaller area than the substrate on all of the plurality of pixels, and the end portion may be an end portion of the scintillator.

The radiation image capturing system may further include a fixing unit that fixes the position of the grid unit to the radiation detector group.

According to the present invention, an effect that it is possible to improve image quality of the radiation image is obtained.

BRIEF DESCRIPTION OF THE DRAWINGS

FIG. 4 is a sectional view of an example of a pixel of a radiation detector of the present embodiment.

FIG. 5 is an illustrative diagrams for explaining a relationship among a radiation irradiation device, a radiation detector group (radiation detector), and a grid unit of the present embodiment.

FIG. 8 is an illustrative diagram illustrating an enlarged overlapping portion of the radiation detectors in FIG. 7.

DESCRIPTION OF THE PREFERRED EMBODIMENTS

Hereinafter, an example of the present embodiment will be described with reference to the drawings.

Figure 1:
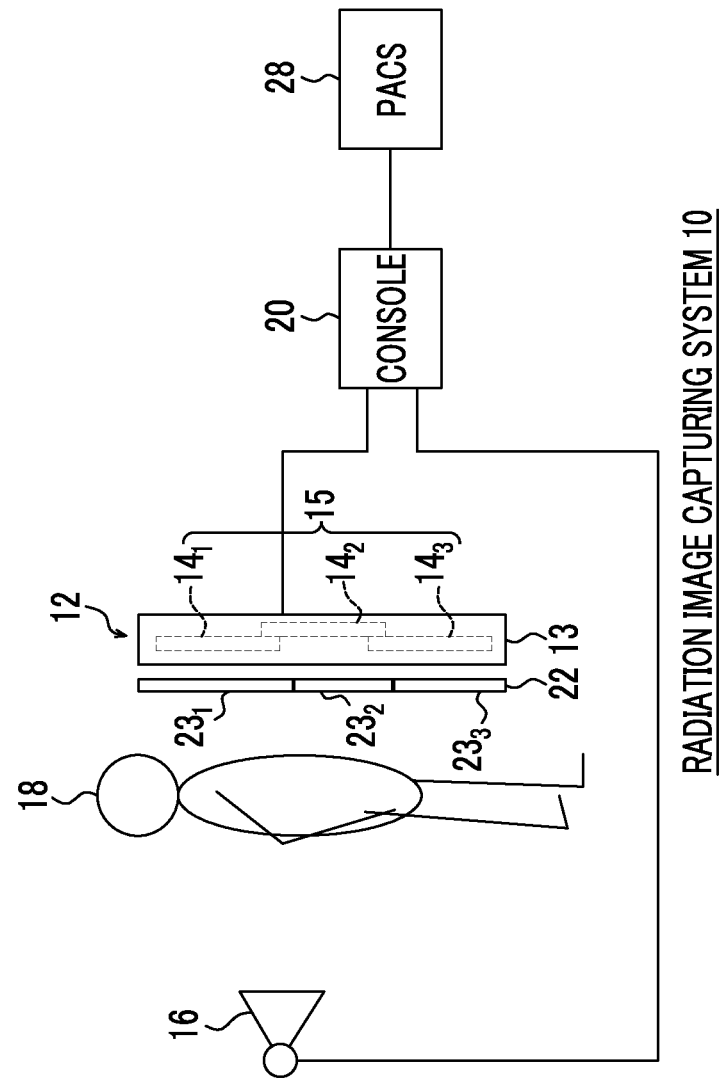
FIG. 1 is a schematic configuration diagram illustrating a schematic configuration of an example of a radiation image capturing system according to the present embodiment.

First, a schematic configuration of an entire radiation image capturing system including a radiation image processing device of the present embodiment will be described. FIG. 1 illustrates a schematic configuration diagram of an entire schematic configuration of an example of the radiation image capturing system of the present embodiment.

The radiation image capturing system 10 of the present embodiment has a function of performing capturing of a radiation image through an operation of a user, such as a doctors or a radiologist, based on, for example, an instruction (photography menu) input from an external system such as an RIS (Radiology Information System) through a console 20.

Further, the radiation image capturing system 10 according to the present embodiment has a function of causing a doctor, a radiologist or the like to interpret a radiation image captured by a cassette 12 by displaying the radiation image on a display unit 34 of the console 20 (see FIG. 2) or a radiation image interpretation device (not shown). Further, the radiation image interpretation device (not shown) is a device having a function of enabling an interpreter to interpret the captured radiation image and is not limited particularly. Examples of the radiation image interpretation device include a so-called interpretation viewer or a display. Further, the radiation image capturing system 10 may display the radiation image on, for example, a PDA (Personal Digital Assistant; not shown) such as a tablet terminal or a smart phone, in addition to the radiation image interpretation device.

The radiation image capturing system 10 according to the present embodiment includes the cassette 12, a radiation irradiation device 16, the console 20, and a grid unit 22.

The radiation irradiation device 16 has a function of irradiating a photography target portion of a subject 18 which is an example of a photography target with a radiation X from a tube (not shown) that is a radiation irradiation source under the control of the console 20. Further, the radiation irradiation device 16 may include an operation input unit for enabling the user to directly manually set irradiation conditions for the radiation X such as a tube voltage, a tube current, and an irradiation time with respect to the radiation irradiation device 16, or a display unit for displaying the set irradiation conditions or the like. Further, the radiation irradiation device 16 transmits information indicating manual setting, manually set setting values, a current status (for example, a standby state, a ready state, during exposure, and exposure end) to the console 20. Further, in the following description, a position of the tube is assumed to be the same as a position of the radiation irradiation device 16.

For the cassette 12 of the present embodiment, a DR (Digital Radiography) cassette is used as a specific example. The cassette 12 includes a radiation detector group 15 in a housing 13. In the present embodiment, a case in which the radiation detector group 15 has three radiation detectors $14_1$ to $14_3$ will be described as a specific example. Hereinafter, in the case where the radiation detectors $14_1$ to $14_3$ are collectively referred to, reference signs indicating the individual radiation detectors are omitted, and the radiation detectors are referred to as a "radiation detector 14". The number of radiation detectors 14 is not limited to the present embodiment.

Further, in the case where the radiation image is captured, capturing of the radiation image is performed in all the radiation detectors 14 by one irradiation (one shot) of the radiation X.

In the present embodiment, the radiation detector 14 is arranged in a position in which an photography region (photography surface) faces the subject 18. Further, in the cassette 12 of the present embodiment, an end portion (a portion) of the radiation detector 14 is arranged to overlap with an end portion of the adjacent radiation detector 14 (which will be described in detail below), as illustrated in FIG. 1.

Since the radiation detector group 15 has a plurality of radiation detectors 14 arranged in this way, an elongated photography region is included in the entire cassette 12.

The cassette 12 is irradiated with the radiation X transmitted through the subject 18 through the grid unit 22.

The grid unit 22 has a function of removing scattered radiation included in the radiation X transmitted through the subject 18. In the grid unit 22 of the present embodiment, a plurality of grids 23 are jointed (which will be described in detail below). A case in which the grid unit 22 includes three grids $23_1$ to $23_3$ will be described as a specific example. Hereinafter, in the case where the grids $23_1$ to $23_3$ are collectively referred to, reference signs indicating the individual grids will be omitted and the individual grids are referred to as an "grid 23". Further, the number of grids 23 is not limited to the present embodiment.

Each radiation detector 14 of the cassette 12 has a function of generating charges according to an amount of the radiation X transmitted through the subject 18 and the grid unit 22, generating image information indicating the radiation image based on the generated amount of charges, and outputting the image information. In the present embodiment, the radiation detector group 15 generating and outputting the image information is referred to as photography.

In the present embodiment, the image information indicating the radiation image output by the cassette 12 is input to the console 20. The console 20 of the present embodiment has a function of performing control of the cassette 12 and the radiation irradiation device 16 using a photography menu, various pieces of information, or the like acquired from an external system or the like over a wireless communication LAN (Local Area Network) or the like. Further, the console 20 of the present embodiment has a function of transmitting or receiving various pieces of information to and from the cassette 12. Further, the console 20 has a function of outputting the radiation image acquired from the cassette 12 to a PACS (Picture Archiving and Communication System) 28. The radiation image captured by the cassette 12 is managed by the PACS 28.

Figure 2:
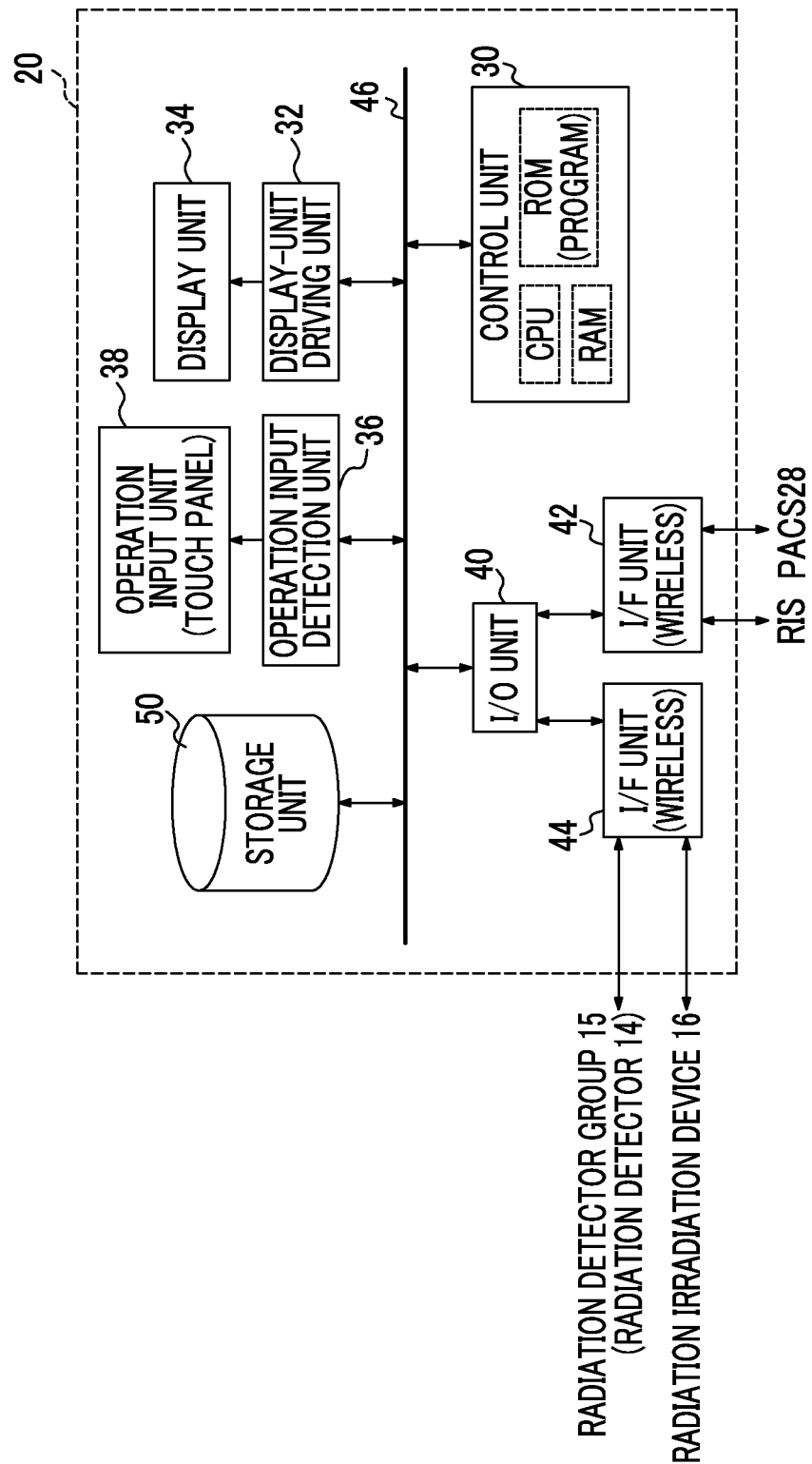
FIG. 2 is a schematic configuration diagram illustrating an example of a console for explaining an image processing function including various corrections of the present embodiment.

The console 20 of the present embodiment is a server computer. FIG. 2 illustrates an example of a schematic configuration diagram of the console 20 for explaining an image processing function including correction of a step image (which will be described in detail below). The console 20 includes a control unit 30, a display-unit driving unit 32, a display unit 34, an operation input detection unit 36, an operation input unit 38, an I/O (Input Output) unit 40, an I/F (Interface) unit 42, an I/F unit 44, and a storage unit 50.

The control unit 30 has a function of controlling an entire operation of the console 20, and includes a CPU (Central Processing Unit), a ROM (Read Only Memory), and a RAM (Random Access Memory). The CPU has a function of controlling the entire operation of the console 20. Various programs including an image processing program used in the CPU, or the like are stored in the ROM in advance. The RAM has a function of temporarily storing various pieces of data. Further, the control unit 30 is an example of a correction unit, and has a function of performing image processing including correction of a step image on the radiation image.

The display-unit driving unit 32 has a function of controlling display of various pieces of information on the display unit 34. The display unit 34 of the present embodiment has a function of displaying the photography menu, the captured radiation image, or the like. The operation input detection unit 36 has a function of detecting an operation state or a processing operation with respect to the operation input unit 38. The operation input unit 38 is used for the user to input a processing operation regarding capturing of the radiation image or image processing of the captured radiation image. The operation input unit 38 may have a form of a keyboard as an example or may have a form of a touch panel integrally formed with the display unit 34. Further, the operation input unit 38 may include a camera, and may have a form in which various instructions are input by causing the camera to recognize a user's gesture.

Further, the I/O unit 40 and the I/F unit 42 have a function of performing transmission or reception of various pieces of information to and from the PACS 28 and the RIS through wireless communication or the like. Further, the I/F unit 44 has a function of performing transmission and reception of various pieces of information to and from the radiation detector 14 of the radiation detector group 15 and the radiation irradiation device 16. Further, the I/O unit 40 and the I/F unit 42 may perform transmission or reception of various pieces of information to and from the PACS 28 and the RIS through wired communication other than the wireless communication.

The storage unit 50 has a function of storing and holding various pieces of data.

The control unit 30, the display-unit driving unit 32, the operation input detection unit 36, the I/O unit 40, and the storage unit 50 are connected to be able to exchange information or the like with each other via a bus 46, such as a system bus or a control bus.

Figure 3:
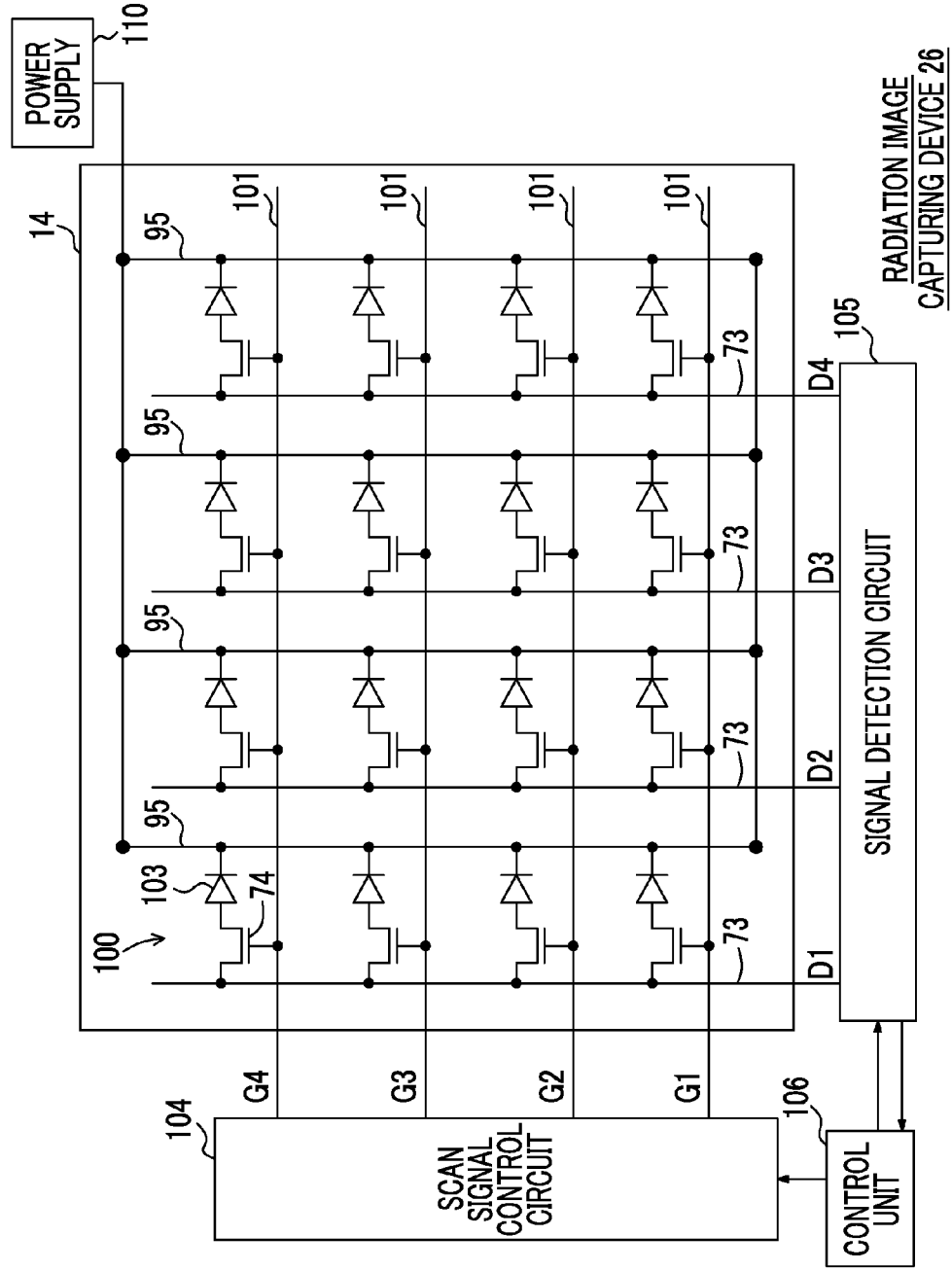
FIG. 3 is a configuration diagram illustrating an example of a configuration of a radiation image capturing device including a radiation detector of the present embodiment.

FIG. 3 illustrates a configuration diagram illustrating an example of a configuration of the radiation image capturing device 26 including the radiation detector 14 of the present embodiment. In the present embodiment, a case in which the present invention is applied to the radiation detector 14 of an indirect conversion scheme that first converts the radiation X such as X rays into light and converts the converted light into charges will be described. Further, a scintillator 98 that converts the radiation into light (see FIG. 4) is not described in FIG. 3.

The radiation detector 14 of the present embodiment is included in the radiation image capturing device 26 together with a scan signal control circuit 104, a signal detection circuit 105, a control unit 106, and a power supply 110. Therefore, the cassette 12 of the present embodiment includes three radiation image capturing devices 26 according to the radiation detector 14.

The radiation detector 14 includes a pixel 100 including a sensor unit 103 that receives light to generate charge and accumulates the generated charge, and a TFT (Thin Film Transistor) switch 74 that is a switch element for reading the charge accumulated in the sensor unit 103. In the present embodiment, the sensor unit 103 is irradiated with the light converted by the scintillator 98 (see FIG. 4), and thus, the charge is generated in the sensor unit 103.

A plurality of pixels 100 are arranged in a matrix form in one direction (gate wiring direction in FIG. 3) and a direction (signal wiring direction in FIG. 3) intersecting with the gate wiring direction. In FIG. 3, a simplified arrangement of the pixels 100 is illustrated but, for example, 1024×1024 pixels 100 are arranged in the gate wiring direction and the signal wiring direction.

Further, a plurality of gate wirings 101 for turning the TFT switches 74 ON/OFF, and a plurality of signal wirings 73 for reading the charge accumulated in the sensor unit 103 are provided to intersect with each other in the radiation detector 14. In the radiation detector 14 of the present embodiment, one signal wiring 73 is provided in each pixel column in one direction, and one gate wiring 101 is provided in each pixel row in an intersecting direction. For example, in the case where 1024×1024 pixels 100 are arranged in the gate wiring direction and the signal wiring direction, 1024 signal wirings 73 and 1024 gate wiring 101 are provided.

Further, a common electrode wiring 95 is provided in parallel with each signal wiring 73 in the radiation detector 14. The common electrode wiring 95 has one end and the other end connected in parallel, and the one end is connected to a power supply 110 that supplies a predetermined bias voltage. The sensor unit 103 is connected to the common electrode wiring 95, and the bias voltage is applied to the sensor unit 103 via the common electrode wiring 95.

A control signal for switching each TFT switch 74 flows through the gate wiring 101. The control signal flows through each gate wiring 101 in this way, and thus, each TFT switch 74 is switched.

An electric signal corresponding to the charge accumulated in each pixel 100 flows through the signal wiring 73 according to a switching state of the TFT switch 74 of each pixel 100. More specifically, the electric signal corresponding to an amount of charge accumulated when the TFT switch 74 of any pixel 100 connected to the signal wiring 73 is turned ON flows through each signal wiring 73.

The signal detection circuit 105 that detects the electrical signal flowing out to each signal wiring 73 is connected to each signal wiring 73. Further, a scan signal control circuit 104 that outputs a control signal for turning the TFT switch 74 ON/OFF to each gate wiring 101 is connected to each gate wiring 101. While FIG. 3 illustrates each of the signal detection circuit 105 and the scan signal control circuit 104 that is simplified as one circuit, a plurality of signal detection circuits 105 and a plurality of scan signal control circuits 104 are provided, and the signal wiring 73 or the gate wiring 101 is connected to every predetermined number (for example, 256) of signal detection circuits 105 and scan signal control circuits 104. For example, in the case where 1024 signal wirings 73 and 1024 gate wirings 101 are provided, four scan signal control circuits 104 are provided and 256 gate wirings 101 are connected to each scan signal control circuit, and similarly, four signal detection circuits 105 are provided and 256 signal wirings 73 are connected to each scan signal detection circuit.

The signal detection circuit 105 includes an amplification circuit (not shown) that amplifies an input electric signal for each signal wiring 73. The signal detection circuit 105 amplifies the electric signal input from each signal wiring 73 using the amplifier circuit, and converts the resultant signal into a digital signal using an ADC (analog-to-digital converter).

The control unit 106 that performs a predetermined process such as noise removal on the digital signal converted by the signal detection circuit 105, outputs a control signal indicating a signal detection timing to the signal detection circuit 105, and outputs a control signal indicating an output timing of the scan signal to the scan signal control circuit 104 is connected to the signal detection circuit 105 and the scan signal control circuit 104.

The control unit 106 of the present embodiment is a microcomputer, and includes, for example, a CPU, a ROM, a RAM, and a nonvolatile storage unit including a flash memory or the like (not shown). The control unit 106 performs control for capturing the radiation image by the CPU executing a program stored in the ROM.

FIG. 4 is a sectional view of the pixel 100 in the radiation detector 14. As illustrated in FIG. 4, the pixel 100 (radiation image capturing device 26) includes a glass substrate 90 and a scintillator 98. As illustrated in FIG. 4, in the glass substrate 90, the gate wiring 101 (see FIG. 3) and a gate electrode 72 are formed on an insulating substrate 71 formed of alkali-free glass or the like. The gate wiring 101 is connected to the gate electrode 72. A wiring layer (hereinafter, also referred to as a "first signal wiring layer") in which the gate wiring 101 and the gate electrode 72 are formed is formed of Al, Cu, or a stacked film mainly including Al or Cu, but the present invention is not limited thereto.

On the first signal wiring layer, an insulating film 85 is formed on one surface, and a portion located on the gate electrode 72 acts as a gate insulating film in the TFT switch 74. The insulating film 85 is formed of, for example, SiNx or the like. The insulating film 85 is formed, for example, using CVD (Chemical Vapor Deposition) film formation.

A semiconductor active layer 78 is formed in an island shape on the gate electrode 72 on the insulating film 85. The semiconductor active layer 78 is a channel portion of the TFT switch 74, and is formed of, for example, an amorphous silicon film.

In a layer on these, a source electrode 79 and a drain electrode 83 are formed. A signal wiring 73 are formed together with the source electrode 79 and the drain electrode 83 in a wiring layer in which the source electrode 79 and the drain electrodes 83 are formed. The source electrode 79 is connected to the signal wiring 73. The wiring layer (hereinafter, also referred to as a "second signal wiring layer"), in which the source electrode 79, the drain electrode 83, and the signal wiring 73 are formed, is formed of Al, Cu, or a stacked film mainly including Al or Cu, but the present invention is not limited thereto. An impurity-doped semiconductor layer (not shown) is formed of impurity-added amorphous silicon or the like between the source electrode 79 and drain electrode 83, and the semiconductor active layer 78. The TFT switch 74 for switching is configured of these. Further, in the TFT switch 74, the source electrode 79 and the drain electrode 83 are reversed according to a polarity of electric charge collected and accumulated by a lower electrode 81 to be described below.

A TFT protection film layer 88 is formed on substantially the entire surface (substantially entire region) of a region in which the pixel 100 on the substrate 71 is provided, in order to cover the second signal wiring layer and protect the TFT switch 74 or the signal wiring 73. The TFT protection film layer 88 is formed of, for example, SiNx or the like. The TFT protection film layer 88 is formed, for example, using CVD film formation.

A coated interlayer insulating film 82 is formed on the TFT protection film layer 88. The interlayer insulating film 82 is formed of a photosensitive organic material having a low dielectric constant (relative dielectric constant $\varepsilon r$=2 to 4) (for example, positive photosensitive acrylic resin: a material obtained by mixing a base polymer including a copolymer of methacrylic acid and glycidyl methacrylate with a naphthoquinonediazide positive photosensitive agent) to a thickness of 1 to 4 μm.

In the glass substrate 90 of the present embodiment, capacitance between metals arranged in layers on and beneath the interlayer insulating film 82 is suppressed to be small by the interlayer insulating film 82. Further, generally, such a material also has a function of a planarization film, and also has an effect that a step of a lower layer is planarized. In the glass substrate 90 of the present embodiment, a contact hole 87 is formed in a position of the interlayer insulating film 82 and the TFT protection film layer 88 that faces the drain electrode 83.

The lower electrode 81 of the sensor unit 103 is formed on the interlayer insulating film 82 so as to cover a pixel region while burying the contact hole 87. The lower electrode 81 is connected to the drain electrode 83 of the TFT switch 74. In the case where a semiconductor layer 91 to be described below is as thick as about 1 μm, a material of the lower electrode 81 is hardly limited as long as the material is a conductive material. Therefore, there is no problem as long as the lower electrode 81 is formed of a conductive metal, such as an Al-based material or ITO (Indium Tin Oxide).

On the other hand, in the case where the thickness of the semiconductor layer 91 is small (approximately 0.2 to 0.5 μm), absorption of light in the semiconductor layer 91 is insufficient. Accordingly, it is preferable to use an alloy mainly including a light-shielding metal or a stacked film in order to prevent an increase in leak current due to the TFT switch 74 being irradiated with light.

The semiconductor layer 91 functioning as a photodiode is formed on the lower electrode 81. In the present embodiment, a photodiode having a PIN structure in which an n+ layer, an i layer, and a p+ layer (n+ amorphous silicon, amorphous silicon, or p+ amorphous silicon) are stacked is adopted as the semiconductor layer 91. The semiconductor layer 91 is formed by sequentially stacking the n+ layer 91A, the i layer 91B, and the p+ layer 91C from a lower layer. The i layer 91B is irradiated with light, and thus, charge (a pair of free electron and free hole) is generated. The n+layer 91A and the p+layer 91C function as a contact layer, and electrically connect the lower electrode 81 and an upper electrode 92 to be described below to the i layer 91B.

The upper electrode 92 is individually formed on each semiconductor layer 91. For the upper electrode 92, for example, a material having a high optically transmissive property, such as ITO or IZO (Indium Zinc Oxide), is used. In the glass substrate 90 of the present embodiment, the sensor unit 103 includes the upper electrode 92 or the semiconductor layer 91, and the lower electrode 81.

On the interlayer insulating film 82, the semiconductor layer 91, and the upper electrode 92, an opening 97A is formed in a portion corresponding to the upper electrode 92, and a coated interlayer insulating film 93 is formed to cover each semiconductor layer 91.

On the interlayer insulating film 93, a common electrode wiring 95 is formed of Al or Cu, or an alloy or a stacked film mainly including Al or Cu. In the common electrode wiring 95, a contact pad 97 is formed in the vicinity of the opening 97A and electrically connected to the upper electrode 92 through the opening 97A of the interlayer insulating film 93.

In the glass substrate 90 formed in this way, a protection layer is also formed of an insulating material having a low light absorption property, as necessary. The scintillator 98 that is a radiation conversion layer is adhered to a surface of the protection film using an adhesive resin having a low light absorption property. Also, the scintillator 98 may be formed using a vacuum deposition method. A scintillator that generates fluorescence having a relatively wide wavelength range, which can generate light having a wavelength region that can be absorbed, is preferred as the scintillator 98. Examples of such a scintillator 98 include CsI:Na, CaWO$_4$, YTaO$_4$:Nb, BaFX:Eu (X is Br or Cl), or LaOBr:Tm, and GOS. Specifically, in the case where imaging is performed using X-rays as the radiation X, it is preferable to include cesium iodide (CsI), and it is particularly preferable to use CsI:Tl (cesium iodide to which thallium is added) or CsI:Na in which an emission spectrum when X-ray is irradiated is 400 nm to 700 nm. Further, an emission peak wavelength of CsI:Tl in a visible light region is 565 nm. Further, in the case where a scintillator including CsI is used as the scintillator 98, it is preferable to use a scintillator that is formed as a strip-shaped columnar crystal structure using a vacuum deposition method.

In the case where the radiation detector 14 adopts a so-called back-surface reading scheme (PSS (Penetration Side Sampling) scheme) in which the radiation detector 14 is irradiated with the radiation X from a side in which the semiconductor layer 91 has been formed, and a radiation image is read by the glass substrate 90 provided on the back surface side of the incidence surface for the radiation X as illustrated in FIG. 4, light is emitted more strongly on the upper surface side of the scintillator 98 provided on the semiconductor layer 91 in FIG. 4. On the other hand, in the case where a so-called surface reading scheme (ISS (Irradiation Side Sampling) scheme) in which the radiation detector 14 is irradiated with the radiation X from the glass substrate 90 side, and the radiation image is read by the glass substrate 90 provided on the surface side of the incidence surface for the radiation X is adopted, the radiation X transmitted through the glass substrate 90 is incident on the scintillator 98, and the glass substrate 90 side of the scintillator 98 emits light more strongly. In the sensor unit 103 of each pixel 100 provided in the glass substrate 90, charge is generated due to the light generated by the scintillator 98. Therefore, in the radiation detector 14, an emission position of the scintillator 98 is close to the glass substrate 90 in the surface reading scheme as compared to the back-surface reading scheme, and thus, resolution of the radiation image obtained through photography is high.

Further, the radiation detector 14 (radiation image capturing device 26) is not limited to the configuration illustrated in FIGS. 3 and 4, and can be variously modified. For example, in the case of the back-surface reading scheme, since the radiation X is less likely to arrive, another imaging device such as a CMOS (Complementary Metal-Oxide Semiconductor) image sensor, which has low resistance to the radiation X, in place of the configuration described above and the TFT may be combined. Further, the radiation detector may be replaced with a CCD (Charge-Coupled Device) image sensor that transfers charge while shifting the charge using a shift pulse corresponding to a gate signal of the TFT.

Further, for example, the radiation detector may have a configuration using a flexible substrate. It is preferable to apply a configuration using, as a base, recently developed ultra-thin glass based on a float method, as the flexible substrate, to improve transmittance of the radiation. Further, the ultra-thin glass that can be applied in this case is disclosed in, for example, "Asahi Glass Co., Ltd., 'Succeeded in development of world's thinnest ultra-thin glass having a thickness of 0.1 mm using a float process', [Online], [Searched for on August 20, 2011], Internet URL:: http//www.agc.com/news/2011/0516.pdf".

Next, the radiation detector group 15 and the grid unit 22 in the radiation image capturing system 10 of the present embodiment will be described in detail. Hereinafter, a case in which the radiation detector 14 using an ISS scheme is used will be described as a specific example. FIG. 5 is an illustrative diagrams for explaining a relationship among the radiation irradiation device 16, the radiation detector group 15 (radiation detector 14), and the grid unit 22. (A) of FIG. 5 illustrates a state when the radiation irradiation device 16, the radiation detector group 15 (radiation detectors 14), and the grid unit 22 are viewed from a side. (B) of FIG. 5 illustrates the radiation detector group 15 (radiation detector 14) viewed from the radiation irradiation device 16 side. Further, (C) of FIG. 5 illustrates the grid unit 22 viewed from the radiation irradiation device 16 side.

As illustrated in (A) of FIG. 5, in the radiation image capturing system 10 of the present embodiment, when the radiation image is captured, the grid unit 22 is arranged on a frame 120. While a manner of arranging the grid unit 22 is not particularly limited, the user detachably sets the grid unit 22 according to a guide 122 provided on the frame 120 in the present embodiment. The cassette 12 (radiation detector group 15) is arranged under the grid unit 22. In the present embodiment, a positional relationship between the grid unit 22 and the cassette 12 is determined by the frame 120 and the guide 122, which are an example of a fixing portion. Further, in the present embodiment, while the cassette 12 is arranged in a space covered with the frame 120 and the grid unit 22, the arrangement of the cassette 12 and the grid unit 22 is not limited to the present embodiment. For example, the frame 120 may not be used and the grid unit 22 may be arranged in contact with the cassette 12 (for example, directly) on the cassette 12.

Figure 6A:
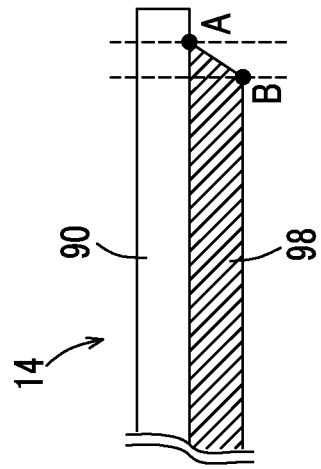
FIGS. 6A and 6B are illustrative diagrams for explaining a photography surface and a step position of the radiation image capturing device according to the present embodiment.
Figure 6B:
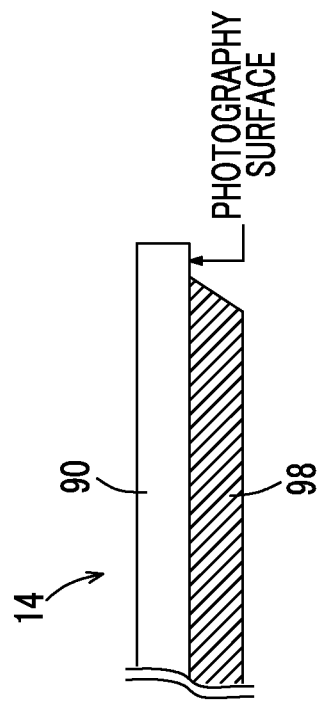

In the radiation detector group 15 of the cassette 12 of the present embodiment, an end portion (a portion) of the photography region of the radiation detector 14 and an end portion of the adjacent radiation detector 14 are arranged to overlap each other, as illustrated in (A) and (B) of FIG. 5, for example, for reasons (1) to (3) below. Specifically, the radiation detectors 14 are overlapped so that the photography regions in the incidence direction of the radiation X (regions of the pixels 100 effective for photography) overlap. Further, in a specific example of the radiation detector 14 of the present embodiment, the glass substrate 90 has a larger area than the scintillator 98, as illustrated in FIGS. 6A and 6B. More specifically, an area facing the radiation irradiation device 16 in the glass substrate 90 is larger than that in the scintillator 98. In the present embodiment, a range (area) of photography region is determined according to the area of the scintillator 98 facing the radiation irradiation device 16. Further, in the present embodiment, since the radiation image capturing device 14 of the ISS scheme is used as an example as described above, the "photography surface" refers to a joint surface of the glass substrate 90 and the scintillator 98, as illustrated in FIG. 6A. Further, in FIGS. 7 and 8, for convenience of illustration, a surface of the radiation image capturing device 14 on the side on which the radiation X is incident is illustrated as the photography surface and used for description.

(1) In the case where a space exists between the photography regions of the respective radiation detectors 14, a non-captured portion may be generated in a captured portion of a subject 18. In this case, an elongated radiation image obtained by connecting the radiation images captured by the radiation detectors $14_1$ to $14_3$ (a radiation image of the entire cassette 12) has defects.

(2) Further, in the case where the radiation detector 14 (radiation image capturing device 26) is mass-produced, it is difficult to arrange the radiation detectors 14 to be in close contact with each other without a gap due to variations in manufacturing of the radiation detector 14 (radiation image capturing device 26).

Further, the radiation detector 14 (radiation image capturing device 26) may be expanded due to temperature. In this case, when the radiation detectors 14 are arranged to be in close contact with each other without a gap, the glass substrate 90 may be damaged.

(3) Further, when the temperature is different between the radiation detectors 14, an expansion rate is different. Therefore, in the cassette 12 of the present embodiment, the respective radiation detectors 14 are fixed to the housing 13, and are arranged without being fixed to each other. Since the radiation detectors 14 are not fixed to each other, the radiation detectors 14 moves.

Further, a range (size) of the photography region of the overlapping portion may be determined according to, for example, the oblique incidence of the radiation X radiated from the radiation irradiation device 16 and the movement of the radiation detector 14.

In the radiation image capturing system 10 of the present embodiment, the position of the radiation irradiation device 16 is movable in a direction along a longitudinal direction of the cassette 12, as illustrated in (A) of FIG. 5. Therefore, according to a photographed portion of the subject 18 (see FIG. 1) to be photographed or a type of photography, the position of the radiation irradiation device 16 or an irradiation angle of the radiation X (an angle of incidence on the radiation detector 14) with respect to the longitudinal direction of the cassette 12 is different, and a relative position with respect to the elongated photography region of the cassette 12 is displaced. Therefore, in each of the radiation detectors 14, the angle of the incident radiation X is different at the same place according to the position of the radiation irradiation device 16.

In the radiation detector group 15 of the cassette 12 of the embodiment, the range of the photography region of the overlapping portion is determined with a margin in consideration of the various cases described above so that the overlap between the photography regions is not eliminated.

Further, as described above, in the radiation detector 14 of the present embodiment, the glass substrate 90 has a larger area than the scintillator 98, and the overlapping portion of the photography region has a smaller area than the overlapping portion of the radiation detector 14 (see the overlapping portion of the detector), as illustrated in (B) of FIG. 5. A shadow of the overlapping portion of the photography region appears as a step image in the radiation image captured by the radiation detector 14 ($14_2$) arranged on the lower side. Specifically, the shadow of the overlapping portion of the photography region is shown in the radiation image captured by the radiation detector 14 ($14_2$) arranged on the lower side. Therefore, densities of the images are different in the step image and an image of another portion (hereinafter referred to as a "normal image"). Further, in the present embodiment, the "step" is generated at a joint between the scintillator 98 and the glass of the radiation image capturing device 14 on the incidence side of the radiation X. A position of the step is due to the end portion of the scintillator 98. For example, in the case where the end portion of the scintillator 98 is oblique as illustrated in FIG. 6B, an intermediate point between the position A and the position B may be the step position. Further, hereinafter, the end portion of the scintillator 98 which is a position of the step, including the intermediate point between the positions A and B, is generically referred to as an "end portion of the scintillator 98".

In a specific example of the radiation detector group 15 of the present embodiment, the end portions overlap in a so-called terrace shape in which the radiation detectors $14_1$ and $14_3$ are on the upper side (an upper side when viewed from the radiation irradiation device 16 side or a side close to the radiation irradiation device 16), and the radiation detector $14_2$ is on the lower side (a lower side when viewed from the radiation irradiation device 16 side or a side far from the radiation irradiation device 16), as illustrated in (A) of FIG. 5.

Therefore, the radiation image captured by the radiation detectors 14 (14$_1$ and 14$_3$) arranged on the upper side is the same as a radiation image captured using a single radiation detector 14, and the step image is not included in the captured radiation image.

Meanwhile, in the radiation detector 14$_2$ arranged on the lower side, a step is generated in a portion overlapping the radiation detector 14 (14$_1$ and 14$_3$) on the upper side, as described above. A shadow of the overlapping portion of the photography region of the radiation detector 14 (14$_1$ and 14$_3$) on the upper side is shown in the captured radiation image, and the step image caused by the step is included.

Further, in the grid unit 22 of the present embodiment, a plurality of grids 23 (23$_1$ to 23$_3$) are jointed as illustrated in (C) of FIG. 5.

In the case where capturing of the radiation image is performed, the radiation X is transmitted through the subject 18, and thus, scattered rays are generated. The grid unit 22 (grid 23) has a function of removing the scattered rays included in the radiation X transmitted through the subject 18. In general, in the grid 23, a thin film of metal such as lead having a high absorption rate of the radiation X, and substance having a low absorption rate of the radiation X that is intermediate substance (inter-space) between the thin films are alternately arranged in a grid density that is as low as, for example, 4.0 lines/mm. Since the radiation X is transmitted through the intermediate substance, for example, aluminum, paper, or a carbon fiber is used as a material of the intermediate substance.

In general, a size (area) of the grid 23 is limited due to, for example, a manufacturing method. For example, since a size of a metal foil such as the lead which absorbs the radiation X or the aluminum as the intermediate substance is limited in manufacturing, the size of the grid 23 is also limited to a size corresponding to the metal foil. Further, use of a silicon semiconductor process is considered as the method of manufacturing the grid 23, but a size that can be processed is limited to a size of a wafer. It is difficult to manufacture a large grid due to such limitations.

Accordingly, in the radiation image capturing system 10 of the present embodiment, the grid unit 22 in which a plurality of grids 23 are jointed to have a desired size is used. Further, the size of each of the plurality of grids 23 used in the grid unit 22 may be the same or may be different.

A method of jointing the grids 23 is not particularly limited. For example, the adjacent grids 23 may be jointed using, for example, adhesion, fusion bonding, and crimping. In the case where the grids are adhered, an adhesive having a transmissive property with respect to the radiation X and not suffering from deformation such as shrink during solidification is preferable. For example, thermosetting adhesive or instantaneous adhesive may be used. Further, a low-melting metal (for example, solder or indium) having a transmissive property with respect to the radiation X may be used instead of the adhesive. Further, for example, the grids 23 may be arranged to be adjacent on a support substrate formed of a material having a transmissive property with respect to the radiation X, such as glass, carbon, and acrylic, and thus, the grids 23 may be jointed. Further, in the case where the grids 23 are jointed, a plurality of grids 23 may be jointed side by side so that the surface is flush as illustrated in FIG. 5 or the like, or may be jointed so that the end portions overlap, as in the radiation detector 14 of the radiation detector group 15 of the present embodiment.

In any case, the grids 23 are jointed, and thus, joints 24$_1$ and 24$_2$ having spacing having a finite length are generated due to an adhesive layer, an air layer, or the like between the grid 23 and the grid 23. The grid unit 22 of the present embodiment has the two joints 24$_1$ and 24$_2$ since three grids 23 are jointed. Specifically, the grid unit 22 has the joint 24$_1$ between the grid 23$_1$ and the grid 23$_2$. Further, the grid unit 22 has the joint 24$_2$ between the grid 23$_2$ and the grid 23$_3$. Hereinafter, in the case where the joints 24$_1$ and 24$_2$ are collectively referred to, a reference sign indicating an individual joint is omitted, and the joints are referred to as a "joint 24". The joint 24 of the present embodiment extends in a strip shape along the step (the end portion) of the radiation detector 14, as illustrated in FIG. 5. In other words, the joint 24 extends in a strip shape in a direction intersecting the longitudinal direction of the radiation detector group 15. Further, specifically, the position of the joint 24 in the present embodiment (a position in a longitudinal direction of the radiation detector group 15) is a position of a center in the longitudinal direction of the radiation detector group 15, of the joint 24 extending in the strip shape.

Since the joint 24 of the grid unit 22 is projected on the radiation detector group 15 by the radiation X, the joint image caused by the joint 24 of the grid unit 22 is included in the radiation image captured by the radiation detector group 15.

Therefore, the step image and the joint image are included in the radiation image captured by the radiation detector group 15 of the present embodiment. More specifically, in the case where the radiation image is captured, a plurality of pixels 100 of the radiation detector 14 include a pixel 100 that accumulates charge generated by the radiation X transmitted through the step, and a pixel 100 that accumulates charges generated by the radiation X transmitted through the joint. The step image is included in the radiation image captured by the radiation detector 14 (14$_2$) on the lower side, as described above. Meanwhile, the joint image is not necessarily included in the radiation image captured by the radiation detector 14 (14$_2$) on the lower side. However, in the case where the joint 24 is provided near the step of the radiation detector 14 (the end portion of the scintillator 98), both of the step image and the joint image may be included in the radiation image captured by the radiation detector 14 (14$_2$) on the lower side.

The step image is corrected by the control unit 30 of the console 20, as described above. The correction of the step image performed by the control unit 30 of the console 20 of the present embodiment will be described. Further, in the present embodiment, the control unit 30 of the console 20 has a function of a correcting unit that performs correction of the step image, but the present invention is not limited thereto. For example, the cassette 12 may have the function of the correction unit. In this case, the radiation image in which the step image has been corrected by the cassette 12 is output from the cassette 12 to the console 20.

Since the step image is included in the radiation image captured by the radiation detector 14 (14$_2$) on the lower side, the correction of the step image is performed on the radiation image captured by the radiation detector 14 (14$_2$) on the lower side.

Further, a method by which the control unit 30 recognizes whether the radiation image acquired from the radiation detector group 15 is an image captured by the radiation detector 14 on the upper side or the lower side is not particularly limited. For example, each radiation detector 14 may add information indicating whether the radiation detector 14 is the radiation detector on the upper side or the lower side to the radiation image, and output the resultant radiation image to the console 20.

In the case where the step image is corrected, the control unit 30 first detects the position of the step image from the radiation image. Since the position of the step image in the radiation image is different according to the angle of incidence of the radiation X on the radiation detector 14, the control unit 30 of the present embodiment detects the position of the step image from the captured radiation image. Further, in the case of the radiation image capturing system 10 in which the control unit 30 cannot obtain the position of the radiation irradiation device 16 or the incidence angle of the radiation X, the position of the step image is detected from the captured radiation image.

A method of detecting the position of the step image is not particularly limited. In a specific example, the control unit 30 of the present embodiment detects the position of the boundary between the step image and the normal image by detecting the straight line (an image indicating the straight line) from the radiation image, and detects the position of the step image based on the detected position of the boundary. Further, hereinafter, the boundary between the step image and the normal image is simply referred to as a "boundary".

The method of detecting a straight line is not particularly limited, and a general scheme may be used. For example, Hough transformation may be used. Further, the method of detecting the position of the step image from the position of the boundary is not particularly limited. For example, an image from the position of the boundary to a predetermined end portion of the radiation image may be detected as the step image.

When the position of the boundary is detected from the radiation image, a process of detecting the position of the boundary may be performed on the entire radiation image, but in the present embodiment, a region estimated to include the position of the boundary is set as the search range, and search is performed in the search range to detect the position of the boundary. The search range may be, for example, a search range in which the position of the step image (position of the boundary) in the radiation image can be acquired in design or through an experiment or the like. Further, in the control unit 30 of the present embodiment, the search range is a range determined based on the incidence angle of the radiation X radiated from the radiation irradiation device 16 to the radiation detector group 15 (radiation detector 14), a thickness of the radiation detector 14, and a distance between the overlapping radiation detectors 14 (which will be described in detail below). Thus, in the case where the position of the boundary is detected from the search range, it is possible to improve detection accuracy as compared to a case in which the position of the boundary is detected from the entire radiation image. Further, in the case where the position of the boundary is detected from the search range, it is possible to shorten a detection time as compared to the case in which the position of the boundary is detected from the entire radiation image.

When the position of the step image is detected, the control unit 30 performs correction of the step image included in the radiation image. The control unit 30 of the present embodiment performs the correction of the step image by performing correction to reduce a density difference between density of the step image and density of a normal image. Further, the control unit 30 can more accurately perform the step correction by performing, for example, offset correction, gain correction, and defective pixel correction prior to the correction to reduce the density difference.

In the correction of the step image performed by the control unit 30 in this way, in the case where search is performed in the search range to detect the position of the boundary, the correction of the step image may not be properly performed if the joint image caused by the joint 24 of the grid 23 is shown in the search range. For example, the control unit 30 may erroneously detect the joint image as the position of the boundary. In the case where the erroneous detection occurs in this way, the position of the step image is erroneously detected, and thus, correction accuracy of the step image is degraded. Therefore, image quality of the corrected radiation image is degraded.

Therefore, in the radiation image capturing system 10 of the present embodiment, the joint 24 of the grid 23 is provided in a position in which the joint image caused by the joint 24 of the grid 23 is not shown in the search range of the position of the boundary. The position of the joint 24 in the grid 23 of the present embodiment will be described in detail. Further, in the present embodiment, the search range is an example of a first region, and the joint image is an example of a second region, but the present invention is not limited thereto. The first region may be a larger region as long as the first region includes the search range. Further, the second region may be a larger region as long as the second region is a region including the joint image.

A specific example of the joint $24_1$ between the grid $23_1$ and the grid $23_2$ will be described in detail with reference to FIGS. 7 and 8. The joint $24_1$ is projected on the radiation detector $14_2$, and a joint image caused by the joint $24_1$ is included in the radiation image captured by the radiation detector $14_2$.

A case in which a position of the step image caused by the step of the radiation detector $14_1$ (the end portion of the scintillator 98) is most deviated due to oblique incidence of the radiation X, as compared to a case in which the radiation X is vertically incident, is considered. FIG. 7 is an illustrative diagram illustrating a case in which a position of the step image (boundary) caused by the step of the radiation detector $14_1$ is most deviated due to oblique incidence of the radiation X. Further, FIG. 8 is an illustrative diagram illustrating an enlarged overlapping portion of the radiation detector $14_1$ and the radiation detector $14_2$ in FIG. 7. Further, a "longitudinal direction" in the following description refers to a longitudinal direction of the radiation detector group 15.

Figure 7:
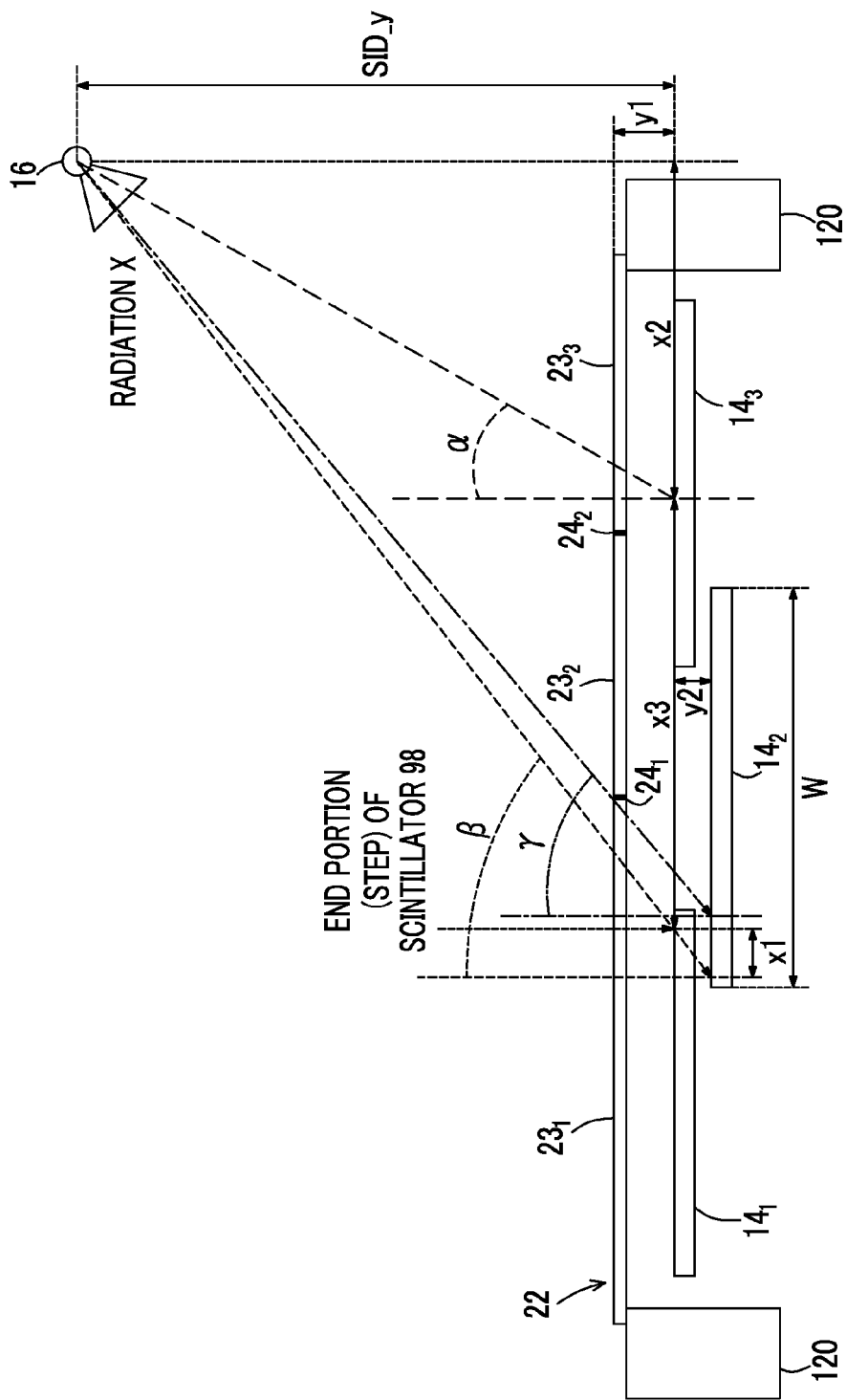
FIG. 7 is an illustrative diagram illustrating a case in which a position of a step image (boundary) caused by a step of the radiation detector of the present embodiment is most deviated due to oblique incidence of radiation X.

A case in which the position of the step image (boundary) is most deviated will be described, and an incidence angle in the case where the radiation X is obliquely incident on a center of the photography region of the radiation detector $14_3$ as illustrated in FIG. 7 is an incidence angle α. In this case, a case in which the subject 18 on the radiation detector $14_3$ is irradiated with the radiation X at an irradiation angle α is assumed. Further, the irradiation angle α is an angle determined according to a photographed portion of the subject 18 or a type of photography. In the case where the irradiation angle α has been obtained in advance, the obtained value may be used. Further, in the case where the value has not been obtained, for example, the angle may be a steepest angle among the angles determined according to the photographed portion or the type of photography.

It is assumed that the angle of incidence of the radiation X on the step of the radiation detector $14_1$ in the case where the radiation X is obliquely incident on the center of the photography region of the radiation detector $14_3$ at the incidence angle α is β, and the angle of incidence on the joint $24_1$ is γ. Further, a distance between the photography surface of the radiation detector $14_1$ and the photography surface of the radiation detector $14_2$ is assumed as y2. In other words, y2 is assumed as a value obtained by adding a thickness of the radiation detector $14_1$ to a distance between the radiation detector $14_1$ and the radiation detector $14_2$. Further, in the present embodiment, a thickness of the radiation image capturing device 14 is defined by the glass substrate 90 and the scintillator 98.

A deviation xl of the position of the boundary is expressed by Equation (1).

$$x1 = y2 \times \tan\beta \tag{1}$$

As shown in Equation (1), the position of the boundary is deviated tanβ×y2 toward a side away from the radiation irradiation device 16 in a longitudinal direction. Hereinafter, a direction away from the radiation irradiation device 16 in a longitudinal direction is referred to as a "+" direction, and a direction approaching the radiation irradiation device 16 is referred to as a "−" direction.

Here, tanβ is obtained using Equations (2) and (3) below. When a distance in a direction vertical to the photography surface from the photography surface of the radiation detector $14_1$ ($14_3$) to the radiation irradiation device 16 (a distance in a vertical direction in FIG. 7) is SID_y, a distance x2 in a longitudinal direction from the center of the photography region of the radiation detector $14_3$ to the radiation irradiation device 16 is expressed by Equation (2) below.

$$x2 = SID\_y \times \tan\alpha \tag{2}$$

Further, when the distance in a longitudinal direction from the step of the radiation detector $14_1$ to the center of the photography surface of the radiation detector $14_3$ is x3, tanβ is expressed by Equation (3) below.

$$\tan\beta = (x2+x3)/SID\_y = (SID\_y \times \tan\alpha + x3)/SID\_y \tag{3}$$

Further, in the case where a length in a longitudinal direction of the overlapping portion between the radiation detectors 14, and a distance between the step and the end portion of the radiation detector 14 is smaller than the length in a longitudinal direction of the radiation detector 14, the distance x3 can be approximated to Equation (4) below when the length in the longitudinal direction of the radiation detector 14 is W.

$$x3 \approx 1.5W \tag{4}$$

In this case, Equation (3) above is expressed as Equation (5) below.

$$\tan\beta = (SID\_y \times \tan\alpha + 1.5\ W)/SID\_y \tag{5}$$

The search range for searching for the position of the boundary is determined based on a maximum amount of deviation of the position of the boundary (the value based on Equation (1) described above). Further, in the radiation image capturing system 10 of the present embodiment, in the case where the cassette 12 (radiation detector group 15) is arranged so that the radiation detector $14_1$ and the radiation detector $14_3$ are reversed in the longitudinal direction, the search range is determined on the assumption that the radiation detector $14_1$ is arranged on the right side, and the radiation detector $14_3$ is arranged on the left side, specifically, in the case illustrated in FIG. 7. Therefore, the search range of the boundary is ±tanβ×y2 in the longitudinal direction from the position of the boundary projected in the case where the radiation X is emitted perpendicularly to the step of the radiation detector $14_1$. Further, since the position of the boundary projected in the case where the radiation X is emitted perpendicularly to the step of the radiation detector $14_1$ can be regarded to be the same as the position of the step of the radiation detector $14_1$, the search range of the boundary can be replaced with ±y2×tanβ in the longitudinal direction from the position of the step of the radiation detector $14_1$.

In the radiation image capturing system 10 of the present embodiment, the joint $24_1$ of the grid unit 22 may not be projected in the search range. Therefore, a case in which the joint $24_1$ is projected on the photography surface of the radiation detector $14_2$ deviated y2×tanβ in a longitudinal direction from the position of the boundary projected in the case where the radiation X is emitted perpendicularly to the step of the radiation detector $14_1$ is considered. A position of the photography surface of the radiation detector $14_2$ deviated y2×tanβ2 in a longitudinal direction from the position of the boundary is assumed to be z.

Further, a distance from the surface of the grid $23_1$ (grid unit 22) on which the radiation X is incident to the photography surface of the radiation detector $14_1$ is assumed to be y1. In other words, y1 is a value obtained by adding a thickness of the grid $23_1$ in the incidence direction to a distance between the grid $23_1$ and the radiation detector $14_1$.

Further, when a distance from a position z to a position of the joint image projected in the case where the radiation X is emitted perpendicularly to the joint $24_1$ is x4, the distance x4 is expressed by Equation (6) below. The position of the joint image in this case is considered to be the same as the position of the joint $24_1$.

$$x4 = (y1+y2) \times \tan\gamma \tag{6}$$

Thus, the position of the joint $24_1$ in this case is a position away by a distance expressed by Equation (7) below in the longitudinal direction from the position of the step of the radiation detector $14_1$.

$$x1+x4 = y2 \times \tan\beta + (y1+y2) \times \tan\gamma \tag{7}$$

Further, tanγ is expressed by Equation (8) below.

$$\tan\gamma = (x2+x3-x1)/SID\_y \tag{8}$$

Equation (8) is expressed by Equation (9) below when approximation in Equation (4) is used.

$$\tan\gamma = (SID\_y \times \tan\alpha + 1.5W - y2 \times \tan\beta)/SID\_y \tag{9}$$

In the case where the position of the step of the radiation detector $14_1$ and the position of the joint $24_1$ are sufficiently away from the radiation irradiation device 16, β can be approximated as β≅γ and tanβ can be approximated as tanβ≅tanγ.

In this case, Equation (7) can be expressed as Equation (10) below.

$$x1+x4 = (y1+2 \times y2) \times \tan\beta \tag{10}$$

As seen from Equation (10), when the position of the joint $24_1$ is away ±(y1+2×y2)×tanβ or more from the position of the step of the radiation detector $14_1$, the joint $24_1$ is not projected in the search range. That is, the joint image caused by the joint $24_1$ is not included in the search range of the radiation image captured by the radiation detector $14_1$.

Further, when the joint $24_2$ is away ±(y1+2×y2)×tanβ or more from the position of the radiation detector $14_3$ similarly to the joint $24_1$, the joint $24_2$ is not projected in the search range.

Accordingly, in the radiation image capturing system 10 of the present embodiment, the joint $24_1$ of the grid 23 in the grid unit 22 is provided in the position away ±(y1+2×y2)×tanβ or more from the position of the step of the radiation detector $14_1$, and the joint $24_2$ is provided in the position away $\pm(y1+2\times y2)\times\tan\beta$ or more from the position of the radiation detector $14_3$.

Thus, in the radiation image capturing system 10 of the present embodiment, since the position of the joint 24 is determined in consideration of the displacement of the angle of incidence of the radiation X on the grid unit 22 and the radiation detector group 15, the joint image caused by the joint 24 can be prevented from being included in the search range of the position of the boundary in the radiation image captured by the radiation detector 14.

Accordingly, it is possible to accurately detect the position of the boundary, and thus, accurately detect the position of the step image. Therefore, it is possible to improve the correction accuracy of the step image, and improve the image quality of the radiation image.

Further, it is preferable to obtain an amount of deviation of the image of the joint 24 experimentally or through calculation or the like in consideration of the deviation of the grid unit 22 or each grid 23 in the longitudinal direction or the thickness of the grid 23, and to provide the location of the joint 24 (distance away from the step) in consideration of the obtained deviation amount.

Figure 9A:
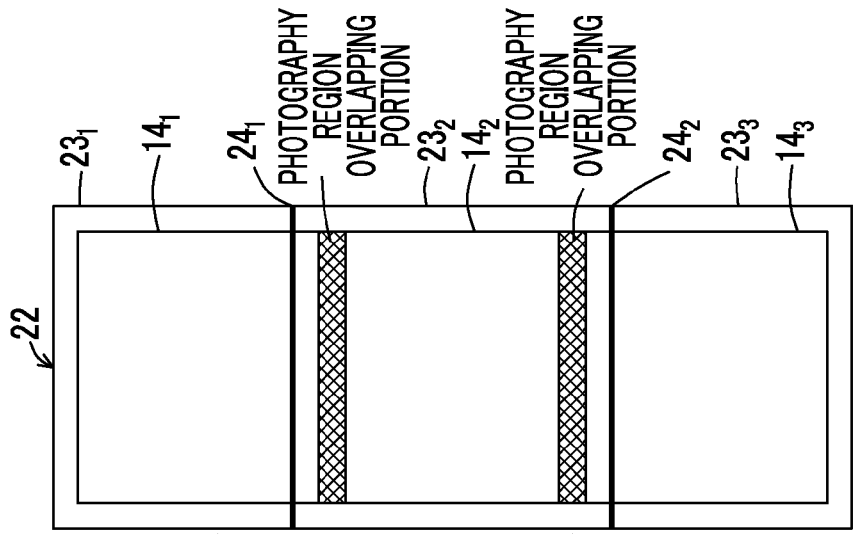
FIGS. 9A to 9C are illustrative diagrams for explaining another specific example of a position of a joint of a grid in a grid unit of the present embodiment.
Figure 9B:
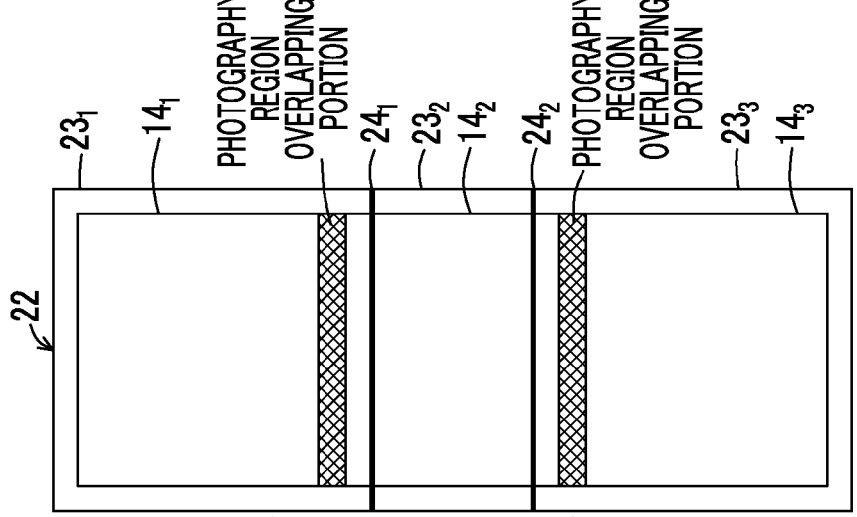
Figure 9C:
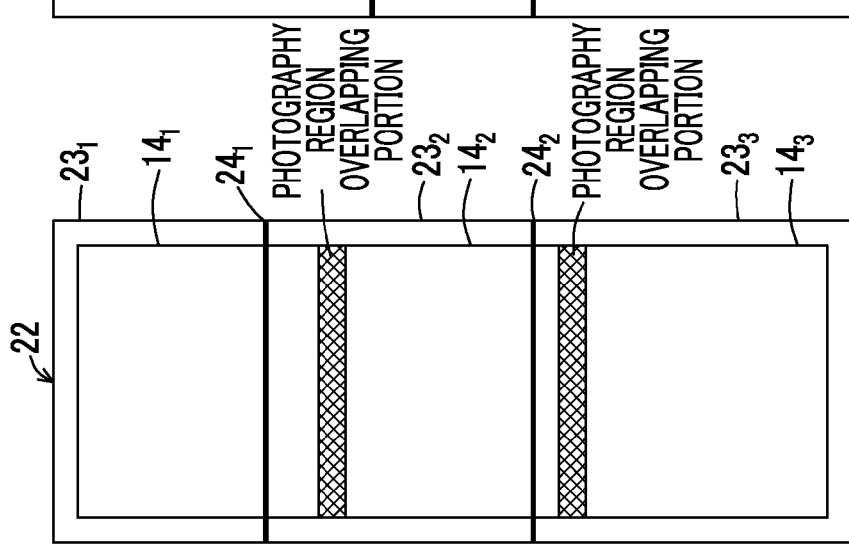

The position of the joint 24 of the grid 23 in the grid unit 22 is not limited to the present embodiment. FIGS. 9A to 9C are illustrative diagrams for explaining other specific examples of the position of the joint 24 of the grid 23 in the grid unit 22. FIG. 9A illustrates a case in which the joint $24_1$ is provided on the radiation detector $14_1$, and the joint $24_2$ is provided on the radiation detector $14_2$. FIG. 9B illustrates a case in which the joints $24_1$ and $24_2$ are provided on the radiation detector $14_2$. Further, FIG. 9C illustrates a case in which the joint $24_1$ is provided on the radiation detector $14_1$, and the joint $24_2$ is provided on the radiation detector $14_3$. Thus, even in the case where the position of the joint 24 is different from that in the present embodiment, the position of the joint 24 is the same as in the present embodiment with respect to the position of the step in each radiation detector 14.

Further, in the radiation detector group 15 of the present embodiment, the radiation detectors $14_1$ and $14_3$ are provided on the side close to the radiation irradiation device 16, and the radiation detector $14_2$ is provided on the side far from the radiation irradiation device 16, but the arrangement of the radiation detector 14 is not limited to the present embodiment. For example, the radiation detectors $14_1$ and $14_3$ may be provided on the side far from the radiation irradiation device 16, and the radiation detector $14_2$ may be provided on the side close to the radiation irradiation device 16. Further, the radiation detector 14 may be arranged stepwise. For example, the radiation detector $14_1$ may be arranged on the side closest to the radiation irradiation device 16, and the radiation detector $14_3$ may be arranged on the side farthest from the radiation irradiation device 16.

Figure 10:
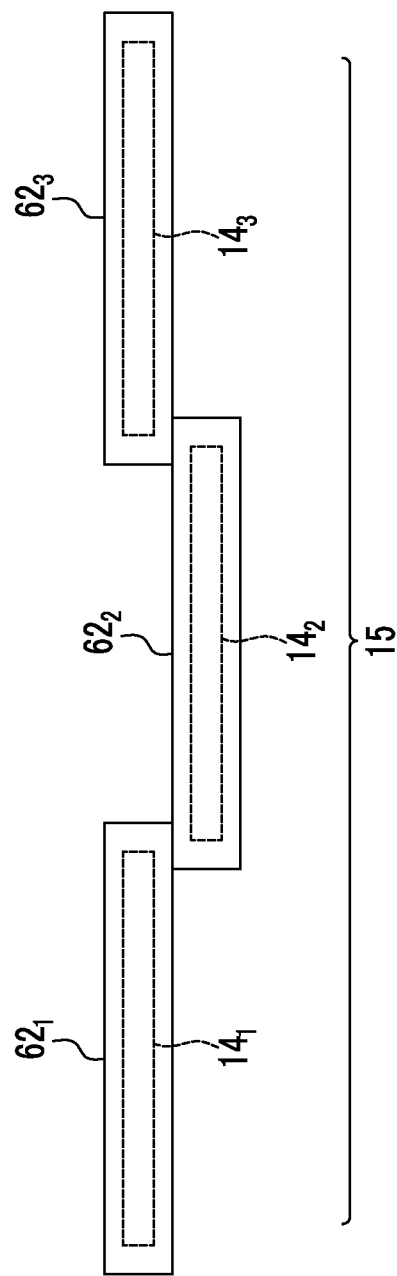
FIG. 10 is an illustrative diagram for explaining a case in which a cassette includes one radiation detector.

Further, the case in which the plurality of radiation detectors 14 (radiation detector group 15) are included in the cassette 12 has been described in the present embodiment, but the present invention is not limited thereto. For example, a plurality (for example, 3) of cassettes 62 including one radiation detector 14 may be included, as illustrated in FIG. 10. In this case, the radiation detector group 15 is formed of the radiation detector 14 included in each cassette 62.

Further, for example, in the case where the position of the radiation irradiation device 16, the irradiation angle of the radiation X, and the position of the step of the radiation detector 14 are obtained, by using the positions and the angle, the console 20 may calculate the position in which the joint 24 in the grid unit 22 is provided using, for example, Equations (1) to (10) described above, and report the calculated position of the joint 24 to, for example, the user. Further, in this case, the console 20 may report the position in which the joint 24 is provided or may report a position in which the joint 24 is not provided.

Further, for example, in the case where the position of the radiation irradiation device 16, the irradiation angle of the radiation X, the position of the step of the radiation detector 14, and the position of the joint 24 are obtained, by using the positions and the angle, the console 20 may determine whether the position of the joint 24 is appropriate (or the joint is projected in the search range of the step image), and report a result of the determination to the user. For example, the console 20 calculates the position of the joint image caused by the joint 24 using Equation (7) or (10) based on the position of the radiation irradiation device 16, the irradiation angle of the radiation X, the position of the step of the radiation detector 14, and the position of the joint 24. Further, the console 20 calculates the search range of the step image ($\pm\tan(\beta\times y2)$ from Equation (1) described above). Also, the console 20 determines whether the position of the joint image is included in the search range. In the case where the position of the joint image is included in the search range, the console 20 alerts this to the user. As the alert, for example, the console 20 may request re-installation of the grid unit 22 (grid 23). In the case where the re-installation is performed, any of the grid unit 22 and the radiation detector group 15 may be moved. In the case where the re-installation is performed in this way, the console 20 may report the position in which the joint 24 is provided or may report a position in which the joint 24 is not provided, as described above. Further, in the case where photography is performed in a state in which the position of the joint image is included in the search range, information indicating this fact may be attached to the radiation image. Further, a correction method in the case where the step image is corrected may be different from a normal method (the method described above in the present embodiment).

Further, the case in which the cassette 12 is a DR cassette has been described in the present embodiment, but the present invention is not limited thereto. The cassette 12 may be a CR cassette. In the case where the cassette 12 is a CR cassette, an imaging plate corresponds to an example of the radiation detector. Further, in the case of the DR cassette, the radiation detector is thicker than that in the CR cassette, and thus, the joint of the grid is easily included in the step image (the search range). Therefore, in the case where the cassette 12 is the DR cassette as in the present embodiment, a higher effect is obtained by applying the present invention.

Further, the radiation X in the present embodiment is not particularly limited, and X rays or y rays may be used.

Further, for example, components such as the radiation image capturing system 10, the radiation detector group 15, the radiation detector 14, the console 20, and the grid unit 22 described in the present embodiment are examples, and it is understood that the components can be changed according to a situation without departing from the spirit of the present invention.

What is claimed is:
1. A radiation image capturing system, comprising:
an irradiation unit that irradiates a photography target with radiation;
a grid unit that removes scattered rays included in the radiation transmitted through the photography target, the grid unit including a plurality of jointed grids; and a radiation detector group that has a plurality of radiation detectors arranged side by side in a direction intersecting an incidence direction of the radiation in a state in which end portions of the radiation detectors overlap in the incidence direction, and captures a radiation image according to the radiation, the radiation image including a step image caused by a step with respect to the incidence direction in the end portion, and a joint image caused by a joint of the grid, wherein a position in which the joint of the grid is provided is a position in which a first region including the step image of the radiation image and a second region including the joint image are spaced.

2. The radiation image capturing system according to claim 1, wherein the positions of the first region, and the second region included in the radiation image are determined based on an angle of incidence of the radiation on the radiation detector.

3. The radiation image capturing system according to claim 2, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and the angle of incidence of the radiation on the radiation detector.

4. The radiation image capturing system according to claim 1, wherein the first region is a search range in which a correction unit searches for the radiation image, the correction unit searching a search range of the radiation image to detect a position of the step image and correcting the detected step image.

5. The radiation image capturing system according to claim 4, wherein the correction unit detects the position of the step image based on a position of a boundary between the step image included in the radiation image and an image different from the step image.

6. The radiation image capturing system according to claim 5, further comprising the correction unit.

7. The radiation image capturing system according to claim 5, wherein the search range is determined in advance based on a thickness in the incidence direction of the radiation detector provided on the side close to the irradiation unit in the incidence direction, a distance between the corresponding radiation detector and the radiation detector overlapping the corresponding radiation detector, a position of the step, and the angle of incidence of the radiation on the radiation detector.

8. The radiation image capturing system according to claim 5, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and an angle of incidence of the radiation on the radiation detector.

9. The radiation image capturing system according to claim 4, further comprising the correction unit.

10. The radiation image capturing system according to claim 9, wherein the search range is determined in advance based on a thickness in the incidence direction of the radiation detector provided on the side close to the irradiation unit in the incidence direction, a distance between the corresponding radiation detector and the radiation detector overlapping the corresponding radiation detector, a position of the step, and the angle of incidence of the radiation on the radiation detector.

11. The radiation image capturing system according to claim 9, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and an angle of incidence of the radiation on the radiation detector.

12. The radiation image capturing system according to claim 4, wherein the search range is determined in advance based on a thickness in the incidence direction of the radiation detector provided on the side close to the irradiation unit in the incidence direction, a distance between the corresponding radiation detector and the radiation detector overlapping the corresponding radiation detector, a position of the step, and an angle of incidence of the radiation on the radiation detector.

13. The radiation image capturing system according to claim 12, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and the angle of incidence of the radiation on the radiation detector.

14. The radiation image capturing system according to claim 4, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and an angle of incidence of the radiation on the radiation detector.

15. The radiation image capturing system according to claim 1, wherein a position of the joint of the grid unit is a position based on a thickness of the grid in the incidence direction, a distance from the grid unit to the radiation detector arranged on the side close to the irradiation unit in the incidence direction, a thickness of the radiation detector in the incidence direction, a distance from the corresponding radiation detector to the radiation detector overlapping the corresponding radiation detector, a position of the step, and an angle of incidence of the radiation on the radiation detector.

16. The radiation image capturing system according to claim 1,
wherein the joint extends in a direction along the step.

17. The radiation image capturing system according to claim 1,
wherein the radiation detector group includes
a first radiation detector that captures a radiation image in which the step image is not included; and
a second radiation detector that is arranged in a position farther from the irradiation unit than the first radiation detector, and captures a radiation image including the step image and the joint image.

18. The radiation image capturing system according to claim 1,
wherein each of the radiation detectors includes
a scintillator that converts radiation radiated from the irradiation unit into light;
a sensor unit that generates charge according to an amount of light converted by the scintillator; and
a substrate in which a plurality of pixels are formed, the pixel including a switch element for reading the charge from the sensor unit.

19. The radiation image capturing system according to claim 18,
wherein the scintillator is formed with a smaller area than the substrate on all of the plurality of pixels, and
the end portion is an end portion of the scintillator.

20. The radiation image capturing system according to claim 1, further comprising a fixing unit that fixes the position of the grid unit to the radiation detector group.

* * * * *